(12) United States Patent
Waterson et al.

(10) Patent No.: US 10,214,495 B2
(45) Date of Patent: Feb. 26, 2019

(54) ANTI-MALARIAL AGENTS

(71) Applicants: MMV MEDICINES FOR MALARIA VENTURE, Geneva (CH); UNIVERSITY OF CAPE TOWN, Rondebosch (ZA)

(72) Inventors: David Waterson, Macclesfield (GB); Michael John Witty, Dover (GB); Kelly Chibale, Claremont (ZA); Leslie Street, Kenilworth (ZA); Diego Gonzalez Cabrera, Muizenburg (ZA); Tanya Paquet, Kenilworth (ZA)

(73) Assignee: University of Cape Town, Rondebosch (ZA)

( * ) Notice: Subject to any disclaimer, the term of this patent is extended or adjusted under 35 U.S.C. 154(b) by 0 days.

(21) Appl. No.: 15/741,786

(22) PCT Filed: Jul. 12, 2016

(86) PCT No.: PCT/IB2016/054151
§ 371 (c)(1),
(2) Date: Jan. 4, 2018

(87) PCT Pub. No.: WO2017/009773
PCT Pub. Date: Jan. 19, 2017

(65) Prior Publication Data
US 2018/0194741 A1 Jul. 12, 2018

(30) Foreign Application Priority Data
Jul. 13, 2015 (EP) .................................... 15176514

(51) Int. Cl.
| C07D 241/20 | (2006.01) |
| C07D 401/04 | (2006.01) |
| A61K 31/4965 | (2006.01) |
| A61K 31/497 | (2006.01) |
| A61K 45/06 | (2006.01) |
| A61P 33/06 | (2006.01) |

(52) U.S. Cl.
CPC .......... C07D 241/20 (2013.01); A61K 31/497 (2013.01); A61K 31/4965 (2013.01); A61K 45/06 (2013.01); A61P 33/06 (2018.01); C07D 401/04 (2013.01); Y02A 50/411 (2018.01)

(58) Field of Classification Search
CPC ............ A61K 2300/00; A61K 31/4965; A61K 31/497; A61K 45/06; A61P 3/06; C07D 241/20; C07D 401/04; Y02A 50/411
See application file for complete search history.

(56) References Cited

FOREIGN PATENT DOCUMENTS

| WO | 2011/086531 A2 | 7/2011 | |
| WO | 2013/121387 A1 | 8/2013 | |
| WO | WO 2013/121387 * | 8/2013 | .......... C07D 401/01 |

OTHER PUBLICATIONS

West, Anthony R., Solid State Chemistry and Its Applications, Wiley, New York, 1988, 358. (Year: 1988).*
International Search Report for PCT/IB2016/054151 dated Oct. 17, 2016.
Younis, Yassir et al: "Structure-Activity-Relationship Studies around the 2 Amino Group and Pyridine Core of Antimalarial 3,5-Diarylaminopyridines Lead to a Novel Series of Pyrazine Analogues with Oral in Vivo Activity", Journal of Medicinal Chemistry, vol. 56, No. 21, 2013, pp. 8860-8871.
Gonzalez Cabrera, Diego et al: "Structure-Activity Relationship Studies of Orally Active Antimalarial 3,5-Substituted 2-Aminopyridines", Journal of Medicinal Chemistry, vol. 55, No. 24, 2012, pp. 11022-11030.

* cited by examiner

*Primary Examiner* — Erich A Leeser
(74) *Attorney, Agent, or Firm* — Thomas | Horstemeyer, LLP

(57) ABSTRACT

The present invention is related to a use of aminopyrazine derivatives in the manufacture of a medicament for preventing or treating malaria. Specifically, the present invention is related to aminopyrazine derivatives useful for the preparation of a pharmaceutical formulation for the inhibition of malaria parasite proliferation.

17 Claims, No Drawings

ANTI-MALARIAL AGENTS

CROSS-REFERENCE TO RELATED APPLICATION

This application is the 35 U.S.C. § 371 national stage application of PCT Application No. PCT/IB2016/054151, filed Jul. 12, 2016, where the PCT claims priority to and the benefit of, EP Patent Application No. 15176514.6,filed Jul. 13, 2015, both of which are herein incorporated by reference in their entireties.

FIELD OF THE INVENTION

The present invention relates to novel anti-malarial agents. Specifically, the present invention is related to agents useful for the preparation of a pharmaceutical formulation for preventing or treating malaria and methods of their use and manufacture.

BACKGROUND OF THE INVENTION

Malaria is caused by protozoan parasites of the genus *Plasmodium* that infect and destroy red blood cells, leading to fever, severe anemia, cerebral malaria and, if untreated, death. *Plasmodium falciparum* is the dominant species in sub-Saharan Africa, and is responsible for approximately 600,000 deaths each year. The disease burden is heaviest in African children under 5 years of age and in pregnant women. *Plasmodium vivax* causes 25-40% of the global malaria burden, particularly in South and Southeast Asia, and Central and South America. The other three main species that are known to infect humans are *Plasmodium ovale, Plasmodium knowelsi* and *Plasmodium malariae*. Malaria is a disease that is prevalent in many developing countries. Approximately 40% of the world's population lives in countries where the disease is endemic; approximately 247 million people suffer from the disease every year.

Various medications are presently used for the treatment of malaria. However, many of these medications are costly and some exhibit significant toxicity and undesirable side effects in humans. Drugs used for treating malaria include artemisinin and its derivatives (such as artemether or dihydroartemisinin, chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one, 5,7'-dichloro-6'-fluoro-2',3',4',9'-tetrahydro-3'-methyl-,(1'R,3'S)-] (CAS Registry Number: 1193314-23-6), Sulfur, [4-[[2-(1,1-difluoroethyl)-5-methyl[1,2,4]triazolo[1,5-a]pyrimidin-7-yl]amino]phenyl] pentafluoro-] (CAS Registry Number: 1282041-94-4), Morpholine, 4-[2-(4-cis-dispiro[cyclohexane-1,3'-[1,2,4]trioxolane-5',2"-tricyclo[3.3.1.13,7]decan]-4-ylphenoxy)ethyl]-] (CAS Registry Number: 1029939-86-3).

Some aminopyrazine derivatives have been described for the treatment of malaria (WO 2013/121387).

However, the widespread emergence of drug resistance of malaria parasites in many tropical countries has compromised many of the current chemotherapies and there is a continued need for new chemotherapeutic approaches. Accordingly, this invention provides novel potent anti-malarial agents and methodology of treating malaria using novel potent anti-malarial agents.

SUMMARY OF THE INVENTION

The present invention is directed towards novel aminopyrazine derivatives with improved properties such as higher solubility, longer plasma half-life and improved oral bioavailability which are useful in the treatment and/or prophylaxis of malaria, pharmaceutical formulation, use and manufacture thereof.

A first aspect of the invention provides an aminopyrazine derivative according to the invention or a pharmaceutically acceptable salt thereof or a pharmaceutically active is derivative thereof.

A second aspect of the invention relates to an aminopyrazine derivative or a pharmaceutically acceptable salt thereof or a pharmaceutically active derivative thereof according to the invention for use as a medicament.

A third aspect of the invention relates to the use of an aminopyrazine derivative according to the invention or a pharmaceutically acceptable salt thereof or a pharmaceutically active derivative thereof, for the preparation of a pharmaceutical composition for the prevention and/or treatment of malaria.

A fourth aspect of the invention resides in a pharmaceutical formulation comprising at least one aminopyrazine derivative according to the invention or a pharmaceutically acceptable salt thereof or a pharmaceutically active derivative thereof, and a pharmaceutically acceptable carrier, diluent or excipient thereof.

A fifth aspect of the invention relates to an aminopyrazine derivative according to the invention or a pharmaceutically acceptable salt thereof or a pharmaceutically active derivative thereof, for use in the prevention and/or treatment of malaria.

A sixth aspect of the invention resides in a method for preventing and/or treating malaria in a patient. The method comprises administering an aminopyrazine derivative according to the invention or a pharmaceutically acceptable salt thereof or a pharmaceutically active derivative thereof in a patient in need thereof.

A seventh aspect of the invention provides a process for the preparation of an aminopyrazine derivative according to the invention or a pharmaceutically acceptable salt thereof or a pharmaceutically active derivative thereof according to the invention and intermediates thereof.

An eighth aspect of the invention provides intermediates of synthesis of aminopyrazine derivatives according to the invention.

A ninth aspect of the invention provides a method for inactivating parasitic infection in a cell comprising the step of contacting the cell with an effective amount of at least one compound according to the invention.

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "pharmaceutically acceptable salts or complexes" refers to salts or complexes of the compounds according to the invention. Examples of such salts include, but are not restricted, to base addition salts formed by reaction of aminopyrazine derivatives of the invention with organic or inorganic bases such as hydroxide, carbonate or bicarbonate of a metal cation such as those selected in the group consisting of alkali metals (sodium, potassium or lithium), alkaline earth metals (e.g. calcium or magnesium) and ammonium salts.

Are also comprised salts which are formed from acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient is capable of providing directly or indirectly, the activity disclosed herein. The term "indirectly" also encompasses prodrugs which may be converted to the active form of the drug via endogenous enzymes or metabolism. The prodrug is a derivative of the compounds according to the invention and presenting anti-malarial activity that has a chemically or metabolically decomposable group, and a compound that may be converted into a pharmaceutically active compound according to the invention in vivo by solvolysis under physiological conditions. The prodrug is converted into a compound according to the present invention by a reaction with an enzyme, gastric acid or the like under a physiological condition in the living body, e.g. by oxidation, reduction, hydrolysis or the like, each of which is carried out enzymatically. According to a particular embodiment, are included the following prodrugs of the following structures that can be cleaved into compounds of the invention by esterases. These compounds can be produced from compounds of the present invention according is to well-known methods. The term "indirectly" also encompasses metabolites of compounds according to the invention.

The term "metabolite" refers to all molecules derived from any of the compounds according to the present invention in a cell or organism, preferably mammal.

In the context of the present invention are encompassed pharmaceutically acceptable salts, complexes, hydrates, solvates, or polymorphs, tautomers, geometrical isomers, optically active forms and pharmaceutically active derivatives of compounds of the invention. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers. Many organic compounds exist in optically active forms having the ability to rotate the plane of plane-polarized light. In describing an optically active compound, the prefixes D and L or R and S are used to denote the absolute configuration of the molecule about its chiral center(s).

The term "malaria" includes disease and conditions related to an infection by *Plasmodium*.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "effective amount" includes "prophylaxis-effective amount" as well as "treatment-effective amount" and can refer to the amount used as part of a combination. The term "prophylaxis-effective amount" refers to a concentration of compound of this invention that is effective in inhibiting, decreasing the likelihood of the disease by malarial parasites, or preventing malarial infection or preventing the delayed onset of the disease by malarial parasites, when administered before infection, i.e. before, during and/or slightly after the exposure period to malarial parasites.

The term "prophylaxis" includes causal prophylaxis, i.e. antimalarial activity comprising preventing the pre-erythrocytic development of the parasite, suppressive prophylaxis, i.e. antimalarial activity comprising suppressing the development of the blood stage infection and terminal prophylaxis, i.e. antimalarial activity comprising suppressing the development of intra-hepatic stage infection. This term includes primary prophylaxis (i.e. preventing initial infection) where the antimalarial compound is administered before, during and/or after the exposure period to malarial parasites and terminal prophylaxis (i.e. to prevent relapses or delayed onset of clinical symptoms of malaria) when the antimalarial compound is administered towards the end of and/or slightly after the exposure period to malarial parasites but before the clinical symptoms. Typically, against *P. falciparum* infections, suppressive prophylaxis is used whereas against *P. vivax* or a combination of *P. falciparum* and *P. vivax*, terminal prophylaxis is used. According to one embodiment, the malaria parasites are *P. falciparum* and *P. vivax*.

Likewise, the term "treatment-effective amount" refers to a concentration of compound that is effective in treating malaria infection, e.g. leads to a reduction in parasite numbers in blood following microscopic examination when administered after infection has occurred.

The term "subject" as used herein refers to mammals. For examples, mammals contemplated by the present invention include humans and the like.

Compounds

According to one embodiment, is provided an aminopyrazine derivative according to Formula (I):

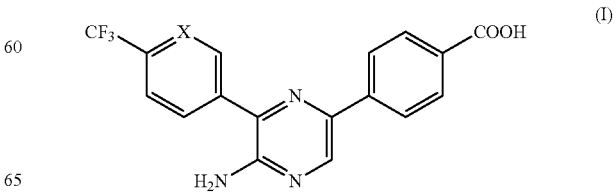

wherein X is CH or N; as well as pharmaceutically acceptable salts, complexes, hydrates, solvates, or polymorphs, tautomers, geometrical isomers, optically active forms, prodrugs and pharmaceutically active derivative thereof.

In a particular embodiment, the invention provides an aminopyrazine derivative according to the invention wherein X is N.

In another particular embodiment, the invention provides an aminopyrazine derivative according to the invention wherein X is CH.

In a particular embodiment is provided an aminopyrazine derivative selected from the following group:4-(5-amino-6-(4-(trifluoromethyl)phenyl)pyrazin-2-yl)benzoic acid; and 4-(5-amino-6-(6-(trifluoromethyl)pyridin-3y1)pyrazin-2-yl) benzoic acid; as well as pharmaceutically acceptable salts, complexes, hydrates, solvates, or polymorphs, tautomers, geometrical isomers, optically active forms and pharmaceutically active derivative thereof.

In a particular embodiment, the aminopyrazine derivative according to the invention is 4-(5-amino-6-(4-(trifluoromethyl)phenyl)pyrazin-2-yl)benzoic acid or a pharmaceutically acceptable salt, complexe, hydrate, solvate, or polymorph, tautomer, geometrical isomer, optically active form or pharmaceutically active derivative thereof. In a particular embodiment, is provided prodrugs of compounds of the invention such of the following Formula (Ia)

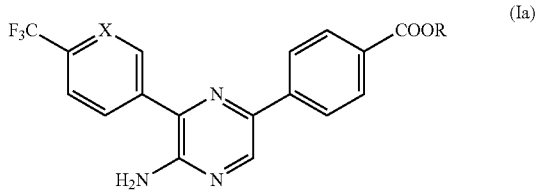

wherein X is CH or N, and R is —CH$_3$, —CH$_2$CH$_3$, —CH(CH$_3$)$_2$, —CH$_2$CH$_2$CH$_2$CH$_3$, —CH$_2$OC(O)C(CH$_3$)$_3$, —C$_6$H$_5$, pCH$_3$O(C$_6$H$_4$)—, —CH$_2$C$_6$H$_5$.

The aminopyrazine derivatives used in the manufacture of a medicament for the prevention or treatment of malaria, are capable of killing and/or inhibiting malaria parasite replication.

Compositions

The invention provides pharmaceutical compositions useful for the prophylaxis or treatment of malaria. The invention further provides methods for treating a mammalian patient, and most preferably a human patient, who is suffering from malaria.

In another particular embodiment, is provided a pharmaceutical formulation containing at least one derivative according to the invention and a pharmaceutically acceptable carrier, diluent or excipient thereof.

In another particular embodiment, is provided a pharmaceutical formulation comprising an aminopyrazine according to Formula (I) and an antimalarial agent as defined in the detailed description.

Pharmaceutical compositions of the invention can contain one or more compound(s) of the invention in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended dosage range to be employed. Compositions according to the invention are preferably oral.

Compositions of this invention may be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Non-aqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in *The Science and Practice of Pharmacy* (*Remington: The Science & Practice of Pharmacy*), 22nd Edition, 2012, Lloyd, Ed. Allen, Pharmaceutical Press, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the *stratum corneum*, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the *stratum corneum*.

The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, transdermally, vaginally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intrathecal, and intra-articular. The compositions of this invention may also be administered in the form of an implant, which allows slow release of the compositions as well as a slow controlled i.v. infusion. In a preferred embodiment, aminopyrazine derivatives according to the invention are administered orally.

This invention is further illustrated by the following examples that are not intended to limit the scope of the invention in any way.

In a particular embodiment, compounds of the invention are administered at a dose to humans of between about 0.1 mg and 5,000 mg such as for example from about 10-1,000 mg.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

The compositions of this invention may be used in a method for inactivating parasitic infection in a cell comprising the step of contacting the cell with an effective amount of at least one compound according to the invention. According to a particular aspect, the cell is a primate cell such as a red blood cell for example a human cell.

Combination

According to the invention, the aminopyrazine derivatives of the invention and pharmaceutical formulations thereof can be administered alone or in combination with a a co-agent useful in the treatment of malaria, such as substances useful in the treatment and/or prevention of malaria e.g. for example a co-agent including, but not limited to, artemisinin or an artemisinin and its derivatives (such as artemether or dihydroartemisinin), chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, doxycycline, atovaquone, proguanil hydrochloride, piperaquine, ferroquine, tafenoquine. arterolane, Spiro[3H-indole-3,1'-[1H]pyrido[3,4-b]indol]-2(1H)-one, 5,7'-dichloro-6'-fluoro-2',3',4',9'-tetrahydro-3'-methyl-,(1'R,3'S)-(CAS Registry Number: 1193314-23-6), Sulfur, [4-[[2-(1,1-difluoroethyl)-5-methyl[1,2,4]triazolo[1,5-a]pyrimidin-7-yl]amino]phenyl] pentafluoro-] (CAS Registry Number: 1282041-94-4), Morpholine,4-[2-(4-cis-dispiro [cyclohexane-1,3'-[1,2,4]trioxolane-5',2''-tricyclo[3.3.1.1$^{3,7}$]decan]-4-ylphenoxy) ethyl]-(CAS Registry Number: 1029939-86-3), [3,3'-Bipyridin]-2-amine, 5-[4-(methylsulfonyl)phenyl]-6'-(trifluoromethyl)-(CAS Registry Number: 1314883-11-8), Ethanone, 2-amino-1-[2-(4-fluorophenyl)-3-[(4-fluorophenyl)amino]-5,6-dihydroimidazo[1,2-a]pyrazin-7(8H)-yl]-(CAS Registry Number 1261109-90-3). The invention encompasses the administration of an aminopyrazine derivative according to the invention or of a pharmaceutical formulation thereof, wherein the aminopyrazine derivatives or the pharmaceutical formulation thereof is administered to an individual prior to, simultaneously or sequentially with other therapeutic regimens or co-agents useful in the treatment of malaria (e.g. multiple drug regimens), in an effective amount. Aminopyrazine derivatives or the pharmaceutical formulations thereof that are administered simultaneously with said co-agents can be administered in the same or different composition(s) and by the same or different route(s) of administration.

Patients

In an embodiment, patients according to the invention are patients suffering from malaria.

In another embodiment, patients according to the invention are patients with a high risk of being infected by *Plasmodium*.

In another embodiment, patients according to the invention are patients with a high risk of being infected by *Plasmodium falciparum*.

In another embodiment, patients according to the invention are patients with a high risk of being infected by *Plasmodium vivax*.

Process of Preparation

In an embodiment according to the invention, is provided a method for preparing a compound of Formula (I) comprising a step of reacting a compound of Formula (5) in the presence of lithium hydroxide monohydrate as follows:

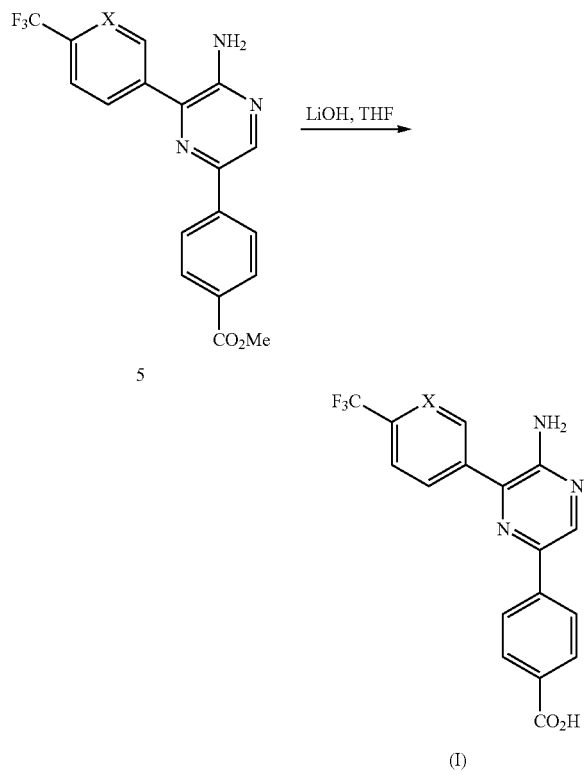

wherein X is CH or N.

In another embodiment, is provided an intermediate for the preparation of a compound of Formula (I), wherein the intermediate is of Formula (5) wherein X is CH or N. In another embodiment, is provided an intermediate of Formula (5) wherein X is CH (Methyl 4-(5-amino-6-(4-(trifluoromethyl)phenyl)pyrazin-2-yl)benzoate)

In another embodiment, is provided an intermediate of Formula (5) wherein X is N (Methyl 4-(5-amino-6-(6-(trifluoromethyl)pyridin-3-yl)pyrazin-2-yl)benzoate).

Use According to the Invention

In one embodiment, the invention provides a use of an aminopyrazine derivative according to Formula (I):

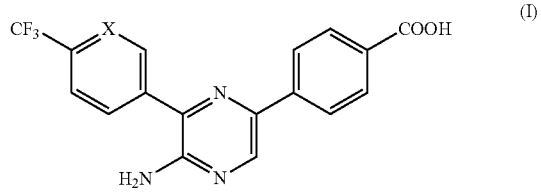

wherein X is CH or N; as well as pharmaceutically acceptable salts, complexes, hydrates, solvates, or polymorphs, tautomers, geometrical isomers, optically active forms and pharmaceutically active derivative thereof for the preparation of a pharmaceutical composition for the treatment or prophylaxis of malaria.

In another embodiment, the invention provides a method for preventing or treating malaria in a patient. The method comprises administering an effective amount of an aminopyrazine derivative according to the invention, or a pharmaceutically acceptable salt or a pharmaceutically active derivative thereof or a pharmaceutical formulation thereof in a patient in need thereof.

In another embodiment, the invention provides an aminopyrazine derivative according to the invention as well as pharmaceutically acceptable salts or a pharmaceutically active derivative thereof or a pharmaceutical formulation thereof, for use in the treatment or prophylaxis of malaria.

In another embodiment, the invention provides a use of an aminopyrazine derivative or a method according to the invention wherein the aminopyrazine derivative is to be administered in combination with a co-agent useful in the treatment of malaria.

In another embodiment, the invention provides a pharmaceutical composition comprising an aminopyrazine derivative according to the invention in combination with a co-agent useful in the treatment of malaria.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims.

In the following the present invention shall be illustrated by means of some examples, which are not to be viewed as limiting the scope of the invention.

EXAMPLES

The Following Abbreviations Refer Respectively to the Definitions Below:

g (gram), h (hour), mmol (millimole), RT (room temperature), DCM (dichloromethane), DMF (N,N-Dimethylformamide), DMSO (Dimethyl Sulfoxide), EDCI (1-Ethyl-3-(3-dimethylaminopropyl)carbodiimide), HOBt (N-Hydroxybenzotriazole), MeOH (methanol), LC (Liquid chromatography), MS (Mass Spectrometry), MHz (Megahertz), NBS (N-bromosuccinimide), NIS (N-Iodosuccinimde), NMR (Nuclear magnetic resonance), TFA (Trifluoroacetic acid), THF (Tetrahydrofuran), TLC (Thin layer chromatography), Et$_2$O (diethylether), UV (Ultraviolet).

The compounds of invention have been named according to the IUPAC standards used in the program ChemBioDraw Ultra (Version 14.0).

The MS and NMR data provided in the examples described below were obtained as followed: LCMS analyses were done on a single quadrupole Agilent instrument with multimode ESI and APCI ionization sources. Either an Atlantis dC18 (50×4.6 mm-5 μm) or Zorbax C18 (50×4.6 mm-5 μm) column was used with a mobile phase of 0.1% formic acid in acetonitrile and a flow rate of 1.5 mL/min. Injection volumes were 1.5-2 μL. NMR spectra were obtained using Bruker DPX 300 or Bruker AVI and AVIII instruments with 5 mm Dual and 5 mm BBFO probes. Appropriate solvents were used as indicated and chemical shifts are reported as δ (ppm) using the solvent signals as internal standard for H¹ and C¹³ NMR.

Example 1

Synthesis of Compounds According to the Invention

The aminopyrazine derivatives can be prepared from readily available starting materials using methods and procedures known from the skilled person. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. The compounds of the invention are synthesized as described in the general synthetic route, Scheme 1 below wherein X is CH or N.

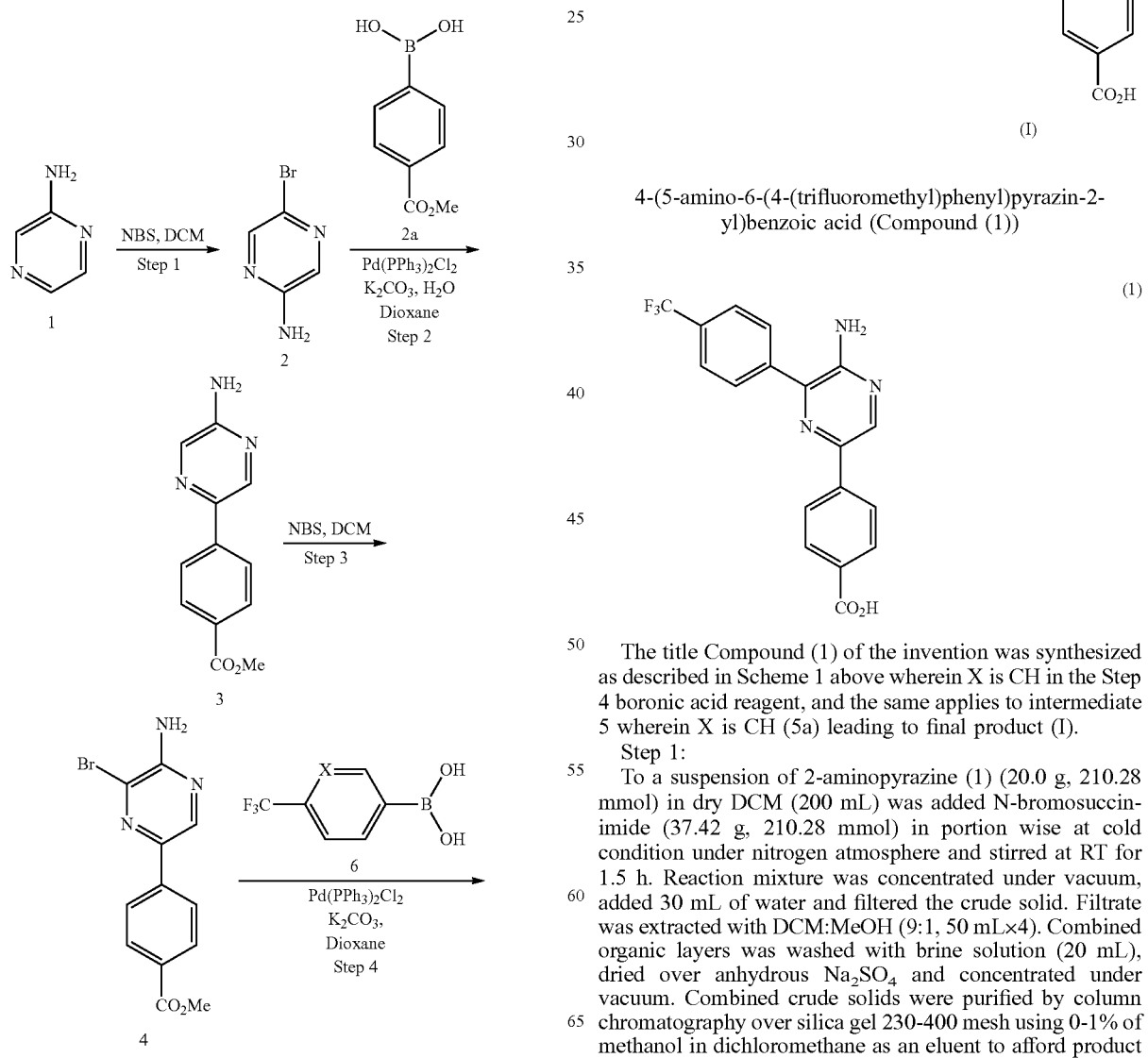

4-(5-amino-6-(4-(trifluoromethyl)phenyl)pyrazin-2-yl)benzoic acid (Compound (1))

The title Compound (1) of the invention was synthesized as described in Scheme 1 above wherein X is CH in the Step 4 boronic acid reagent, and the same applies to intermediate 5 wherein X is CH (5a) leading to final product (I).

Step 1:

To a suspension of 2-aminopyrazine (1) (20.0 g, 210.28 mmol) in dry DCM (200 mL) was added N-bromosuccinimide (37.42 g, 210.28 mmol) in portion wise at cold condition under nitrogen atmosphere and stirred at RT for 1.5 h. Reaction mixture was concentrated under vacuum, added 30 mL of water and filtered the crude solid. Filtrate was extracted with DCM:MeOH (9:1, 50 mL×4). Combined organic layers was washed with brine solution (20 mL), dried over anhydrous Na₂SO₄ and concentrated under vacuum. Combined crude solids were purified by column chromatography over silica gel 230-400 mesh using 0-1% of methanol in dichloromethane as an eluent to afford product 2 (19.0 g, 52.7%) as yellow solid. ¹H NMR (400 MHz, DMSO-d6): δ 8.03 (d, J=1.28 Hz, 1H), 7.68 (d, J=1.32 Hz, 1H), 6.66 (s, 2H). LC-MS APCI: Calculated for C$_4$H$_4$BrN$_3$: 174.00; Observed m/z [M+H]$^+$176.00.

Step 2:

To the stirring solution of 2 (50 g, 287 mmol) in 1,4-dioxane (1250 mL) was added 4-methoxycarbonyl phenyl boronic acid (2a) (56.89 g, 316 mmol) followed by 1M aqueous solution of potassium carbonate (575 mL, 574 mmol) at RT and purged with N$_2$ gas for 40 minutes. Bis(triphenylphosphine)palladium(II)chloride (14.12 g, 20.12 mmol was added to the reaction mixture. The reaction mixture was heated to reflux temperature for 4 h. After completion of the reaction (Confirm by TLC) the reaction mixture was cooled to RT and filtered through a bed of celite. The bed was washed with ethyl acetate (3×300 mL). Organic layer was separated and aqueous layer was re extracted with ethyl acetate (2×400 mL). The combined organic layer was washed with water, dried over sodium sulfate and concentrated under vacuum. The crude material was purified by column chromatography over silica gel (230-400 mesh) using 3.5% of MeIH in DCM as an eluent to afford 3 (39.1 g, 57%) as yellow solid.

Step 3:

To the stirring suspension of 3 (30 g, 130.71 mmol) in dry DCM (300 mL) was added N-bromo succinimide (25.59 g, 143.79 mmol) in portion wise at 0° C. under nitrogen atmosphere and stirred at RT for 1 h. After completion of the reaction (Confirm by TLC) the reaction mixture was quenched with water (5 mL) and was concentrated under vacuum to afford crude product 4 (40.26 g, crude) as brown solid. The crude product was taken for the next step without further purification.

Step 4:

To the stirring solution of 4 (40.26 g, 130.71 mmol) in 1,4-dioxane (800 mL) was added 3-(trifluoromethyl)phenyl boronic acid (6) (27.31 g, 143.7 mmol) followed by 1M aqueous solution of potassium carbonate (230 mL, 230 mmol) at RT. Reaction mixture was purged with N$_2$ gas for 40 minutes. Bis(triphenylphosphine)palladium(II)chloride (6.4 g, 9.1 mmol) was added to the reaction mixture and was heated to reflux temperature for 4 h. After completion of the reaction (Confirm by TLC) the RM was cooled to RT and filtered through a bed of celite. The bed was washed with ethyl acetate (4×500 mL). Organic layer was separated and aqueous layer was re extracted with ethyl acetate (2 X 500 mL). The combined organic layer was washed with water, dried over sodium sulfate and concentrated under vacuum. The crude material was purified by column chromatography over silica gel (230-400 mesh) using 25-30% of EtOAc in petroleum ether as an eluent to afford 5a (25.5 g, 52.2%) as yellow solid.

Step 5:

To the stirring solution of 5a (60.0 g, 160.6 mmol) in THF: Water: MeOH [5:2:3] (600 mL) was added lithium hydroxide monohydrate (26.7 g, 643 mmol) at 0° C. and stirred for 16 h. After completion of the reaction (Confirm by TLC) the Reaction mixture was concentrated under vacuum. The crude was acidified to pH ~2 with 1.5 N HCl and stirred or 5 h (to ensure complete conversion from carboxylate salt to free acid). The yellow solid that appeared was filtered under suction. The crude solid was washed thoroughly with water (7×600 mL). The solid obtained was suspended in 1000 mL of water and stirred for 1 h and filtered under suction (12 h). The solid was purified by washing with DCM: MeOH [(3:97); 6×800 mL] followed by Et$_2$O (2×700 mL) and pentane (2×600 mL) to afford Compound (1) of the invention (35.5 g, 61.7%) as pale yellow solid.

An alternative synthesis of Compound (I) is shown in Scheme 2 below wherein X is CH or N.

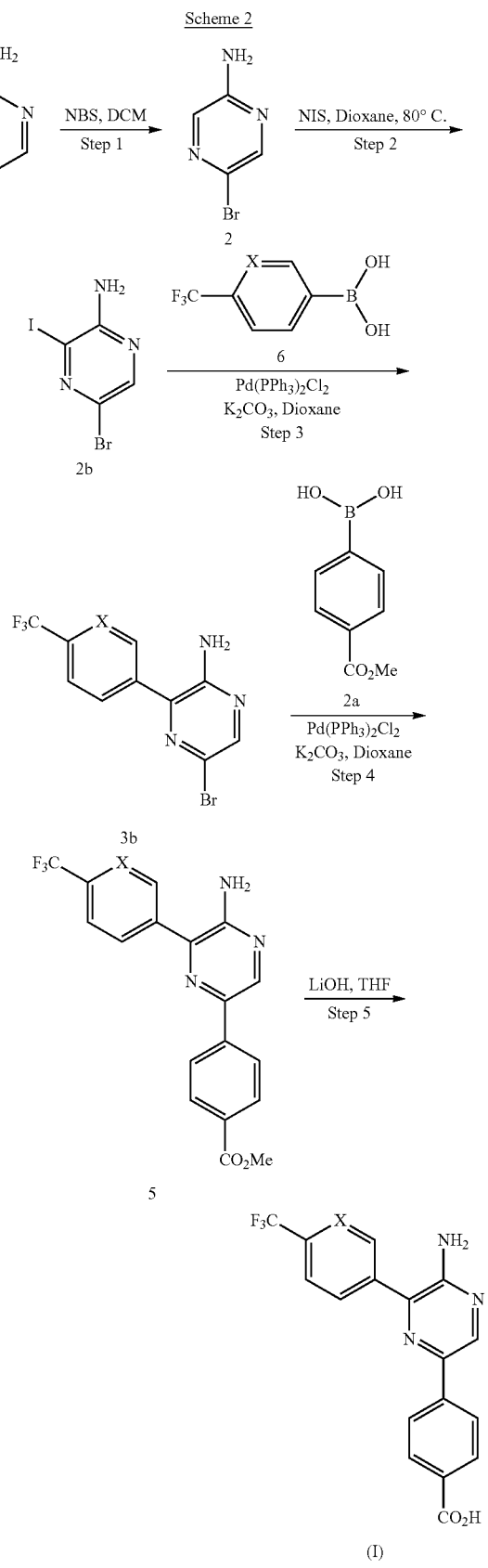

Step 1:

To a suspension of 2-aminopyrazine (1) (20.0 g, 210.28 mmol) in dry DCM (200 mL) was added N-bromosuccinimide (37.42 g, 210.28 mmol) portion wise under cold conditions and under nitrogen atmosphere and stirred at RT for 1.5 h. Reaction mixture was concentrated under vacuum, added 30 mL of water and filtered the crude solid. Filtrate was extracted with DCM:MeOH (9:1, 50×4). Combined organic layers was washed with brine solution (20 mL), dried over anhydrous $Na_2SO_4$ and concentrated under vacuum. Combined crude solids were purified by column chromatography over silica gel 230-400 mesh using 0-1% of methanol in dichloromethane as an eluent to afford product 2 (19.0 g, 52.7%) as yellow solid. $^1$H NMR (400 MHz, DMSO-d6): δ 8.03 (d, J=1.28 Hz, 1H), 7.68 (d, J=1.32 Hz, 1H), 6.66 (s, 2H). LC-MS APCI: Calculated for $C_4H_4BrN_3$: 174.00; Observed m/z [M+H]$^+$176.00.

Step 2:

To the solution of 2 (10.0 g, 57.47 mmol) in 1,4-dioxane (100 mL) was added N-iodosuccinimide (15.5 g, 68.96 mmol). The reaction mixture was heated to 800 C for 16 h, cooled to RT and concentrated under vacuum to remove 1,4-dioxane. 50 mL of water was added and extracted with dichloromethane (50 mL×4), washed with water (20 mL×3), dried over sodium sulfate and concentrated under reduced vacuum. Crude product was purified by flash chromatography using 20-30% ethyl acetate in petroleum ether to afford compound 2b (4.3 g, 25.1%). $^1$H NMR (400 MHz, DMSO-d6): δ 8.05 (s, 1H), 6.76 (s, 2H).

Step 3:

To a solution of 2b (4.0 g, 13.33 mmol) in 1,4-dioxane (55 mL) was added 3-(trifluoromethyl)phenyl boronic acid (6) (2.79 g, 14.67 mmol) followed by 1M aqueous solution of potassium carbonate (26.6 mL, 26.67 mmol) at RT. Reaction mixture was purged with $N_2$ gas for 30 minutes. Bis(triphenylphosphine)palladium(II)chloride (0.65 g, 0.93 mmol) was added to the reaction mixture and was heated to reflux for 4 h, cooled to RT, filtered through celite. Filtrate was concentrated under vacuum to remove dioxane. 50 mL of water was added and extracted with dichloromethane. Organic layer combined and washed with water, dried over sodium sulfate and concentrated under vacuum. Crude product purified by flash chromatography using 30% ethyl acetate in petroleum ether to afford compound 3b (3.5 g, 83.3%) as pale yellow solid. $^1$H NMR (400 MHz, DMSO-d6): δ 8.14 (s, 1H), 7.90 (d, J=8.40 Hz, 2H), 7.84 (d, J=8.40 Hz, 2H), 6.63 (s, 2H). LC-MS APCI: Calculated for $C_{11}H_7BrF_3N_3$: 318.10; Observed m/z [M+H]$^+$: 318.0.

Step 4:

To a solution of compound 3b (3.0 g, 9.43 mmol) in 1,4-dioxane (37 mL) was added 4-methoxy carbonyl phenyl boronic acid (2a) (1.87 g, 10.37 mmol) at RT and purged with $N_2$ gas for 30 minutes. Bis(triphenylphosphine)palladium(II)chloride (0.46 g, 0.66 mmol) and 1 M aqueous solution of potassium carbonate (18.8 mL, 18.86 mmol, pre-purged with $N_2$ gas) were added to the reaction mixture. The reaction mixture was heated to reflux for 4 h and cooled to RT and then filtered through celite. Filtrate was concentrated under vacuum to remove dioxane. 50 mL of water was added and extracted with dichloromethane. Organic layers were combined and washed with water, dried over sodium sulfate and concentrated under vacuum. The crude material was purified by column chromatography over silica gel 230-400 mesh using 3.5% of MeOH in DCM as an eluent to afford compound 5 (3.0 g, 85.7%). $^1$H NMR (300 MHz, DMSO-d6): δ 8.72 (s, 1H), 7.85-8.15 (m, 8H), 6.69 (s, 2H), 3.85 (s, 3H). LC-MS APCI: Calculated for $C_{19}H_{14}F_3N_3O_2$: 373.3; Observed m/z [M+H]$^+$: 374.0.

Step 5:

To the solution of compound 5 (8.0 g, 21.43 mmol) in THF (50 mL) was added lithium hydroxide monohydrate [(3.6 g, 85.71 mmol, in water (25 mL)] at RT and stirred for 16 h. Reaction mixture was concentrated under vacuum, added 10 mL of water and citric acid till acidic. Solid was filtered, washed with water (10 mL×3), washed with DCM (10 mL×3) and dried to afford Compound (1) (5.20 g, 68.4%) as pale brown solid. $^1$H NMR (300 MHz, DMSO-d6): δ 8.63 (s, 1H), 7.84-8.03 (m, 8H), 6.48 (s, 2H). LC-MS APCI: Calculated for $C_{18}H_{12}F_3N_3O_2$: 259.3; Observed m/z [M+H]$^+$: 360.2. Purity by LC-MS: 99.54%.

4-(5-amino-6-(6-(trifluoromethyl)pyridin-3-yl) pyrazin-2-yl)benzoic acid (Compound (2))

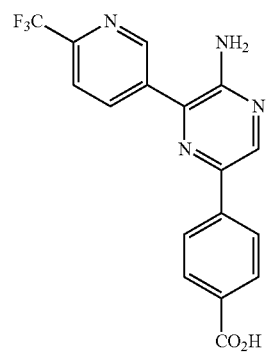

(2)

The title Compound (2) of the invention was synthesized as described in Scheme 1 above wherein X is N in the Step 4 boronic acid reagent 6 (6a), and the same applies to intermediate 5 wherein X is N (5b) leading to final product (I).

Step 1:

To an ice cooled suspension of 2-aminopyrazine (1) (15.0 g, 157.28 mmol) in dry DCM (150 mL) was added N-bromosuccinimide (30.8 g, 210 mmol) in portionwise under nitrogen atmosphere and stirred at RT for 1.5 h. Reaction mixture was concentrated under vacuum, added 30 mL of water and filtered the crude solid. Filtrate was extracted with DCM (50 mL×4) and the combined organic layers was washed with brine solution (100 mL), dried over anhydrous $Na_2SO_4$ and concentrated under vacuum. Combined crude solids were purified by column chromatography over silica gel 230-400 mesh by using 10-20% of ethyl acetate in petroleum ether as an eluent to afford product 2 (16.0 g, 59.2%) as pale yellow solid. $^1$H NMR (400 MHz, DMSO-d6): δ 8.03 (s, 1H), 7.67 (s, 1H), 6.65 (s, 2H). LC-MS APCI: Calculated for $C_4H_4BrN_3$ 174.00; Observed m/z [M+H]$^+$ 176.00 Purity by LC-MS: 98.8%.

Step 2:

To a solution of 2 (25.0 g, 143.0 mmol) in 1,4-dioxane (100 mL) was added 4-methoxycarbonyphenylboronic acid (2a) (28.5 g, 158.0 mmol) followed by potassium carbonate (39.6 g, 287.0 mmol) in water 290 mL (1M solution) at RT. Reaction mixture was purged with $N_2$ gas for 15 min. Bis(triphenylphosphine) palladium(II)chloride (7.06 g, 10.02 mmol) was added to the reaction mixture. The reaction mixture was heated to reflux for 5 h, cooled to RT and concentrated under vacuum to remove dioxane. Residue was extracted with EtOAc (100 mL×3). Combined organic layers was washed with brine solution (100 mL), dried over anhydrous $Na_2SO_4$ and concentrated under vacuum. Combined crude solids were purified by column chromatography over silica gel 230-400 mesh by using 40% of ethyl acetate in petroleum ether as an eluent to afford compound 3 (15 g, 45.6%) as pale yellow solid. $^1H$ NMR (300 MHz, DMSO-d6): δ 8.60 (s, 1H), 8.06 (d, J=8.58, 2H), 7.96-7.99 (m, 3H),6.75 (s, 2H), 3.85 (s, 3H). LC-MS APCI: Calculated for $C_{12}H_{11}N_3O_2$ 229.23; Observed m/z $[M+H]^+$230.2. Purity by LC-MS: 98.29%.

Step 3:

To a cold suspension of compound 3 (15 g, 65.0 mmol) in dry DCM (300 mL) was added N-bromosuccinimide (11.6 g, 65.0 mmol) portionwise under nitrogen atmosphere and stirred at RT for 30 min. To the reaction mixture was added 200 mL of water and extracted with DCM (100 mL×2). Combined organic layers was washed with brine solution (200 mL), dried over anhydrous $Na_2SO_4$ and concentrated under vacuum. Crude material was purified by column chromatography over silica gel 230-400 mesh using 20-30% of ethyl acetate in petroleum ether as an eluent to afford compound 4 (6.0 g, 30%) as pale yellow solid. $^1H$ NMR (400 MHz, DMSO-d6): δ 8.71 (s, 1H), 8.00-8.07 (m, 4H), 7.08 (s, 2H), 3.87 (s, 3H).

Step 4:

To a solution of compound 4 (6.0 g, 19.0mmol) in 1,4-dioxane (100 mL) was added 2-(trifluoromethyl)pyridine-5-boronic acid (6a) (4.08 g, 21.0 mmol) at RT and purged with $N_2$ gas for 30 minutes. Bis(triphenylphosphine) palladium(II)chloride (0.95 g, 13.0 mmol) and 1M aqueous solution of potassium carbonate (39 mL, 38.0 mmol, pre-purged with $N_2$ gas) were added to the reaction mixture. The reaction mixture was heated to reflux for 5 h and cooled to RT. Reaction mixture was concentrated under vacuum, added 30 mL of water and filtered the crude solid. Filtrate was extracted with DCM (50 mL×2). Combined organic layers was washed with brine solution (100 mL), dried over anhydrous $Na_2SO_4$ and concentrated under vacuum. Combined crude solids were purified by column chromatography over silica gel 230-400 mesh by using 20% of ethyl acetate in petroleum ether as an eluent to afford 5b (6.0 g, 82.4%) as pale yellow is solid. $^1H$ NMR (400 MHz, DMSO-d6): δ 9.14 (s, 1H), 8.77 (s, 1H), 8.45 (d, J=8.0 Hz, 1H), 8.16 (d, J=8.4 Hz, 2H), 8.00-8.05 (m, 3H), 6.87 (s, 2H), 3.86 (s, 3H). LC-MS APCI: Calculated for $C_{18}H_{13}F_3N_4O_2$ 374.32; Observed m/z $[M-H]^+$373. Purity by LC-MS: 96.78%.

Step 5:

To the solution of compound 5b (6.0 g, 16 mmol) in THF (60 mL) was added lithium hydroxide monohydrate (1.34 g, 32.0 mmol) in water (15 mL) at RT and stirred for 4 h. Reaction mixture was concentrated under vacuum, added 10 mL of water and citric acid till acidic. Solid was filtered, washed with water (10 mL×3), dried and again washed with ethanol followed by diethyl ether and dried to afford Compound (2) (5.1 g, 88.4%) as white solid. $^1H$ NMR (400 MHz, DMSO-d6): δ 9.15 (s, 1H), 8.76 (s, 1H), 8.47 (dd, J=1.78 & 8.04 Hz, 1H), 7.98-8.11 (m, 5H), 6.81 (s, 2H). $^{13}C$ NMR (100 MHz, DMSO-$d_6$) δ: 45.11, 120.84, 121.16, 123.57, 125.12, 130.23, 132.23, 134.41, 137.18, 138.42, 139.50, 140.61, 146.38, 150.19, 153.43, 168.11, 172.05, 177.94. LC-MS APCI: Calculated for $C_{17}H_{11}F_3N_4O_2$ 360.30; Observed m/z $[M-H]^+$359. Purity by LC-MS: 99.80%.

If the above synthetic methods are not applicable to obtain aminopyrazine derivatives according to the invention and/or necessary intermediates, suitable methods of preparation known by a person skilled in the art should be used. In general, the synthesis pathways for any individual derivative will depend on the specific substituents of each molecule and upon the ready availability of intermediates necessary; again such factors being appreciated by those of ordinary skill in the art. For all the protection and deprotection methods, see Philip J. Kocienski, in "*Protecting Groups*", Georg Thieme Verlag Stuttgart, 2005 and Theodora W. Greene and Peter G. M Wuts in "*Protective Groups in Organic Synthesis*", Wiley Interscience, $4^{th}$ Edition 2006. Compounds of this invention can be isolated in association with solvent molecules by crystallization from evaporation of an appropriate solvent. The pharmaceutically acceptable acid addition salts of the aminopyrazine derivatives, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of an aminopyrazine derivative with a suitable base. Both types of salts may be formed or interconverted using ion-exchange resin techniques.

Example 2

Anti-Malarial Activities of Compounds According to the Invention

The ability of aminopyrazine derivatives according to the invention to kill *P. falciparum* parasites and/or to inhibit its proliferation is assayed through their ability to inhibit *Plasmodium falciparum* growth. Compounds were screened against multidrug resistant (K1) and sensitive (NF54) strains of *P. falciparum* in vitro as described by *Vennerstrom et al.* 2004, *Nature*, 430, 900-904.

Example 3

Solubility of Compounds According to the Invention

Kinetic solubility was performed using 10 mM stock solutions of each compound in 100% DMSO. Dilutions were prepared to a theoretical concentration of 200 μM (n=2) in phosphate buffered saline (PBS) pH 6.5 (in 2% DMSO), in 0.01 M HCl pH 2 (in 2% DMSO) and in biologically relevant gastrointestinal media, fasted state simulated intestinal fluid, FaSSIF (in 2% DMSO). Calibration curves (11-220 μM) were prepared in DMSO. All dilutions were equilibrated at room temperature and mixed for 2 hours on an orbital shaker. The concentration of the test compounds was determined by HPLC using a Kinetex $C_{18}$ column (2.1 mm×50 mm, 2.6 μm) at a column temperature of 35° C. An injection volume of 5 μL was used with a mobile phase flow rate of 0.6 mL/min. The mobile phase gradient method was as follows in Table 1:

TABLE 1

| Time (min) | % A | % B |
|---|---|---|
| 0.00 | 100 | 0 |
| 0.20 | 100 | 0 |
| 1.40 | 0 | 100 |
| 1.58 | 0 | 100 |
| 1.60 | 100 | 0 |
| 3.00 | 100 | 0 |

Mobile phase A: 0.1% formic acid in 5% acetonitrile/water (v/v) (pH 3.1)

Mobile phase B: 0.1% formic acid in acetonitrile (pH 3.1)

Compound concentration (x) in the PBS/FASSIF/HCl samples was calculated from the peak area (y) in the UV chromatogram by extrapolation from a three point calibration curve using the relationship: y=ax+b, where a is the slope and b is the intercept. Solubility was reported in the range <5-220 µM.

TABLE 2

| Compound | P. fal. NF54 IC$_{50}$ (nM) | P. fal K1 IC$_{50}$ (nM) | PI4KB IC$_{50}$ (µM) | Kinetic Solubility pH 6.5/ Fassif pH6.5 (µM) |
|---|---|---|---|---|
| (1) | 33 | 32 | 7.7 | 180/178 |
| (2) | 26 | 24 | 23 | 187/199 |
| Reference 1 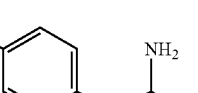 | 13 | 14 | 5.0 | <5/115 |

Those data in Table 2 show that the compounds of the invention have a highly increased solubility as compared to a reference aminopyrazine compound.

Example 4

Pharmacokinetic Data for Compounds of the Invention

Compounds of the invention were tested for their pharmacokinetics in rats according to the protocol below. Two different formulations were used to dose the compound of the invention as described in Table 3 below

TABLE 3

| | Intravenous | Oral |
|---|---|---|
| Dose | 5 mg/kg | 15 mg/kg |
| Formulation | Solution in an aqueous vehicle at pH2 containing 10% dimethyl sulphoxide, 40% (v/v) propylene glycol, 10% (v/v) Ethanol, 0.1% (v/v) Tween 80, sterilized through a 0.22 µM syringe filter. | Suspension in an aqueous vehicle comprising 0.5% (w/v) hydroxypropyl methylcellulose and 0.4% Tween 80. |

Compound (1) was prepared for administration immediately prior to the experiment. The dose was prepared according to the average weight of the animals and an assumed volume of 350 µL of vehicle (IV) or 1000 µL of vehicle (oral). Volumes were adjusted io for each animal's individual weight to dose the compound at 5 mg/kg for the IV group (n=3 rats) and 20 mg/kg to the oral group (n=3). Water was supplied ad libitum, but animals were starved for 12 hours prior to dosing. Food was reinstated 5 hours post-dose.

The orally-treated animals were dosed by gavage with the drug introduced as a bolus. The IV-treated animals were anaesthetized and the drug was administered by infusion over a period of 2 minutes. Doses were staggered to allow for accurately timed sampling. Blood was collected at predetermined time-points to evaluate the kinetic profile over 24-48 hours. Blood sampling schedule, measured in hours post-dose, for the two groups of rats after the administration of Compound (1) are presented in Table 4 below:

TABLE 4

| | Time post-dose (hours) | |
|---|---|---|
| Sample | Oral administration | IV administration |
| 1 | 0 | 0 |
| 2 | — | 0.17* |
| 3 | 0.5 | 0.5 |
| 4 | 1 | 1 |
| 5 | 3 | 3 |
| 6 | 5 | 5 |
| 7 | 8 | 8 |
| 8 | 12 | 12 |
| 9 | 24 | 24 |
| 10 | 32 | 32 |
| 11 | 48 | 48 |

*10 minutes post dose

Whole blood was collected via the tail vein into heparinised microcentrifugation tubes and stored on ice. Within 60 minutes of collection, samples were transferred to a freezer and stored at −80 ° C. until analysis was carried out via LC/MS/MS.

Preparation and Extraction:

The extraction process was carried out on ice. To extract the drug for analysis, 30 µL of whole blood from each sample as well as from a series of standards and quality controls was transferred to a 96-well plate. A volume of 90

µL of cold methanol containing a suitable internal standard (approx. 60 ng/mL was added to each well and the plate was sealed and vortexed vigorously for 60 seconds to precipitate the proteins and release the compounds into the solvent). These were then centrifuged at 10000 G for 10 minutes to pellet the proteins and cellular debris, and the supernatant was transferred to a duplicate 96-well plate. The plate was transferred to the LC/MS/MS and held at 4° C. until all samples were injected onto the column.

LC/MS/MS Analysis:

LC/MS/MS analysis was carried out with 5 µL of each sample, using a method which was developed for simultaneous detection of compound (1) and the internal standard using a Phenomenex Hydro-RP column at 20° C. The mobile phase utilized acetonitrile containing 0.1% formic acid (v/v) as the organic component, and 0.1% (v/v) formic acid in water as the aqueous component. The mobile phase ran as a gradient at 400 µL/min, with the organic component increasing from 5% to 95% over 4 minutes before re-equilibration. The assay was calibrated over the range 2-6250 ng/mL (0.0056 µM-17.44 µM). Results are presented in Table 5 below.

TABLE 5

| Compound | (1) | | (2) | | Reference 1 | |
|---|---|---|---|---|---|---|
| Rat PK: dose (mg/kg) | 5.0 (iv) | 15.0 (po) | 5.0 (iv) | 20.0 (po) | 5.0 (iv) | 20.0 (iv) |
| Apparent $T_{1/2}$ (h) | 4.9 | | 4.4 | | 1.0 | |
| Plasma Cl (ml/min/kg) | 10.1 | | 16.7 | | 39 | |
| Vd (L/kg) | 4.3 | | 6.4 | | 3.5 | |
| Oral Bioavailability (%) | | 94 | | 38 | | 25 |

Those data in Table 5 support that compounds of the invention have longer half-life, lower plasma clearance, higher volume of distribution and better oral bioavailability than aminopyrazine reference 1.

Example 5 hPI4KB Inhibition Selectivity of Compounds According to the Invention

The compounds of the invention were tested on their ability to inhibit the human PI4K kinase. The non-radiometric ADP-Glo™ Assay (Promega, Madison, Wis., USA) was used for measuring the activity of the PI4KB lipid kinase. All kinase assays were performed in 96-well half-area microtiter plates from Greiner Bio-One (Frickenhausen, Germany) in a 25 µl reaction volume. The reaction cocktail was pipetted in 3 steps in the following order:

10 µl of ATP solution (in assay buffer, see below)
5 µl of test sample in 10% DMSO
10 µl of enzyme/substrate mixture PI4KB assay contained 50 mM HEPES-NaOH, pH 7.5, 1 mM EGTA, 100 mM NaCl, 0.03% CHAPS, 2 mM DTT, ATP, 10 µM, PI4KB kinase, 20 ng/25 µL, PI substrate 50 µM. and 3 mM $MnCl_2$.

The reaction cocktails were incubated at 30° C. for 40 minutes. The reaction was stopped with 25 µl ADP-Glo reagent per well. Plates were incubated for 40 minutes at room temperature, followed by addition of 50 µl kinase detection reagent per well and incubation for further 60 minutes at room temperature. Signal was measured with a microplate multilable reader (Victor2, Perkin Elmer, Boston, Mass., USA), in luminescence mode.

All assays were performed with a BeckmanCoulter Biomek 2000/SL robotic system. The median value of the counts (n=8) of each assay plate was defined as "low control". This value reflects unspecific binding of radioactivity to the plate in the absence of a protein kinase but in the presence of the substrate. The median value of the counts in column 7 of each assay plate (n=8) was taken as the "high control", i.e. full activity in the absence of any inhibitor. The difference between high and low control was taken as 100% activity.

As part of the data evaluation the low control value from a particular plate was subtracted from the high control value as well as from all 80 "compound values" of the corresponding plate. The residual activity (in %) for each well of a particular plate was calculated by using the following formula (i):

Res. Activity (%)=100×[(cpm of compound−low control)/(high control−low control)]  (i)

The residual activities for each concentration and the compound $IC_{50}$ values were calculated using Quattro Workflow V3.1.0 (Quattro Research GmbH, Munich, Germany; www.quattro-research.com). The fitting model for the $IC_{50}$ determinations was "Sigmoidal response (variable slope)" with parameters "top" fixed at 100% and "bottom" at 0%. The fitting method used was a least-squares fit. Results are presented under Table 2 above.

The invention claimed is:

1. An aminopyrazine according to Formula (I),

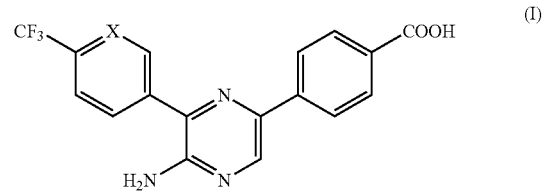

wherein X is CH or N; as well as pharmaceutically acceptable salts, complexes, polymorphs, tautomers, geometrical isomers, and optically active forms thereof.

2. An aminopyrazine according to claim 1 wherein X is N.
3. An aminopyrazine according to claim 1 wherein X is CH.
4. An aminopyrazine according to claim 1, wherein the aminopyrazine is selected from the following group:
4-(5-amino-6-(4-(trifluoromethyl)phenyl)pyrazin-2-yl) benzoic acid; and 4-(5-amino-6-(6-(trifluoromethyl) pyridin-3yl)pyrazin-2-yl)benzoic acid; as well as pharmaceutically acceptable salts, complexes, polymorphs, tautomers, geometrical isomers, and optically active forms thereof.
5. An aminopyrazine according to claim 1, wherein the aminopyrazine is 4-(5-amino-6-(4-(trifluoromethyl)phenyl) pyrazin-2-yl)benzoic acid.
6. An aminopyrazine according to claim 1, wherein the pharmaceutically acceptable salt is selected from Lithium, sodium and ammonium salt.
7. A pharmaceutical formulation containing at least one aminopyrazine according to claim 1, and a pharmaceutically acceptable carrier, diluent or excipient thereof.
8. A pharmaceutical formulation according to claim 7 further comprising an antimalarial agent.
9. A pharmaceutical formulation according to claim 8 wherein the antimalarial agent is selected from artemisinin or an artemisinin and its derivatives (such as artemether or dihydroartemisinin, chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one, 5,7'-dichloro-6'-fluoro-2',3',4',9'-tetrahydro-3'-methyl-,(1'R,3'S)- (CAS Registry Number: 1193314-23-6), Sulfur, [4-[[2-(1,1-difluoroethyl)-5-methyl[1,2,4]triazolo[1,5-a]pyrimidin-7-yl]amino]phenyl] pentafluoro-] (CAS Registry Number: 1282041-94-4), Morpholine,4-[2-(4-cis-dispiro [cyclohexane-1,3'-[1,2,4]trioxolane-5',2"-tricyclo[3.3.1.1$^{3,7}$]decan]-4-ylphenoxy)ethyl]- (CAS Registry Number: 1029939-86-3), [3,3'-Bipyridin]-2-amine, 5-[4-(methylsulfonyl)phenyl]-6'-(trifluoromethyl)- (CAS Registry Number: 1314883-11-8), Ethanone, 2-amino-142-(4-fluorophenyl)-3-[(4-fluorophenyl)amino]-5,6-dihydroimidazo [1,2-a]pyrazin-7(8H)-yl]-(CAS Registry Number 1261109-90-3).

10. An aminopyrazine according to claim 1, or a pharmaceutical formulation thereof for use in the prevention and/or treatment of malaria.

11. An aminopyrazine for use according to claim 10 wherein the aminopyrazine is to be administered in combination with a co-agent useful in the treatment of malaria.

12. An aminopyrazine for use according to claim 11 wherein the antimalarial agent is selected from artemisinin or an artemisinin and its derivatives (such as artemether or dihydroartemisinin, chloroquine, quinine, mefloquine, amodiaquine, atovaquone/proguanil, doxycycline, lumefantrine, piperaquine, pyronaridine, halofantrine, pyrimethamine-sulfadoxine, primaquine, quinacrine, doxycycline, atovaquone, proguanil hydrochloride, piperaquine, ferroquine, tafenoquine, arterolane, Spiro[3H-indole-3,1'-[1H]pyrido[3,4-b]indol]-2(1H)-one, 5,7'-dichloro-6'-fluoro-2',3',4',9'-tetrahydro-3'-methyl-,(1'R,3'S)- (CAS Registry Number: 1193314-23-6), Sulfur, [4[[2-(1,1-difluoroethyl)-5-methyl[1,2,4]triazolo[1,5-a]pyrimidin-7-yl]amino]phenyl]pentafluoro-] (CAS Registry Number: 1282041-94-4), Morpholine, 4-[2-(4-cis-dispiro[cyclohexane-1,3'-[1,2,4]trioxolane-5',2"-tricyclo[3.3.1.1$^{3,7}$]decan]-4-ylphenoxy)ethyl]- (CAS Registry Number: 1029939-86-3), [3,3'-Bipyridin]-2-amine, 5-[4-(methylsulfonyl)phenyl]-6'-(trifluoromethyl)- (CAS Registry Number: 1314883-11-8), Ethanone, 2-amino-142-(4-fluorophenyl)-3-[(4-fluorophenyl)amino]-5,6-dihydroimidazo[1,2-a]pyrazin-7(8H)-yl]-(CAS Registry Number 1261109-90-3).

13. A process for the preparation of an aminopyrazine derivative according to Formula (I) comprising the step of reacting an intermediate of Formula (5) in presence of lithium hydroxide monohydrate as follows:

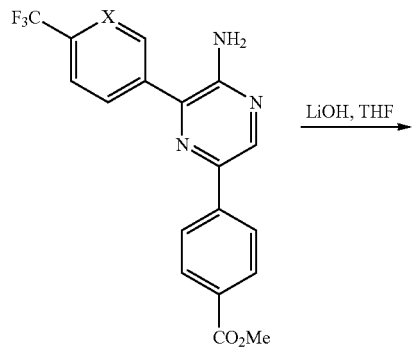

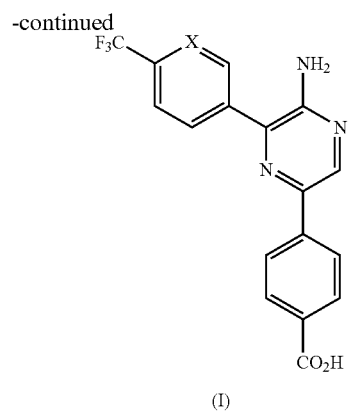

wherein X is CH or N.

14. An intermediate of Formula (5)

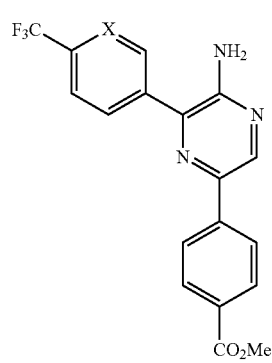

wherein X is CH.

15. An intermediate of Formula (5)

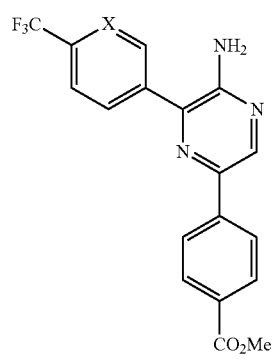

wherein X is N.

16. A method of preventing and/or treating malaria in a patient, wherein the said method comprises administering an aminopyrazine derivative according to claim 1, or a pharmaceutically active derivative thereof in a patient in need thereof.

17. A method for inactivating parasitic infection in a cell comprising the step of contacting the cell with an effective amount of at least one compound according to claim 1, or a pharmaceutically active derivative thereof.

* * * * *